United States Patent [19]

Berger

[11] Patent Number: 4,676,294

[45] Date of Patent: Jun. 30, 1987

[54] GATE

[76] Inventor: Robert P. Berger, 4421 Rochelle Pl., Encino, Calif. 91316

[21] Appl. No.: 766,391

[22] Filed: Sep. 9, 1985

Related U.S. Application Data

[63] Continuation-in-part of Ser. No. 625,302, Jun. 27, 1984, abandoned.

[51] Int. Cl.⁴ ............................................. B22C 9/04
[52] U.S. Cl. .................................... 164/35; 164/244; 164/246; 164/DIG. 4; 433/206
[58] Field of Search .................... 164/DIG. 4, 34, 35, 164/246, 244; 433/206

[56] References Cited

U.S. PATENT DOCUMENTS

| | | | |
|---|---|---|---|
| 1,543,229 | 6/1925 | Nichols | 164/244 |
| 3,320,658 | 5/1967 | Bolda et al. | 228/246 |
| 3,604,496 | 9/1971 | Grosjean | 164/244 |
| 3,970,138 | 7/1976 | Buhrer | 164/244 |
| 4,109,699 | 8/1978 | Miller et al. | 164/244 |
| 4,356,859 | 11/1982 | Savage | 164/244 |
| 4,396,054 | 8/1983 | Cole | 164/34 |

Primary Examiner—Nicholas P. Godici
Assistant Examiner—S. Heinrich
Attorney, Agent, or Firm—Allan M. Shapiro

[57] ABSTRACT

Gate is a wax structure for forming part of a wax master in investment casting of a dental prosthesis. The gate has a square feeder with a circular disc on each end. The square feeder reduces the cracking stresses between adjacent feeders to reduce unwanted fins, and the square shape aids in final cutoff of the cast prosthetic. In the wax master, one of the discs is secured to the prosthetic form and the other disc to the conventional reservoir bar. The disc shape aids in filleting to the form and bar.

28 Claims, 9 Drawing Figures

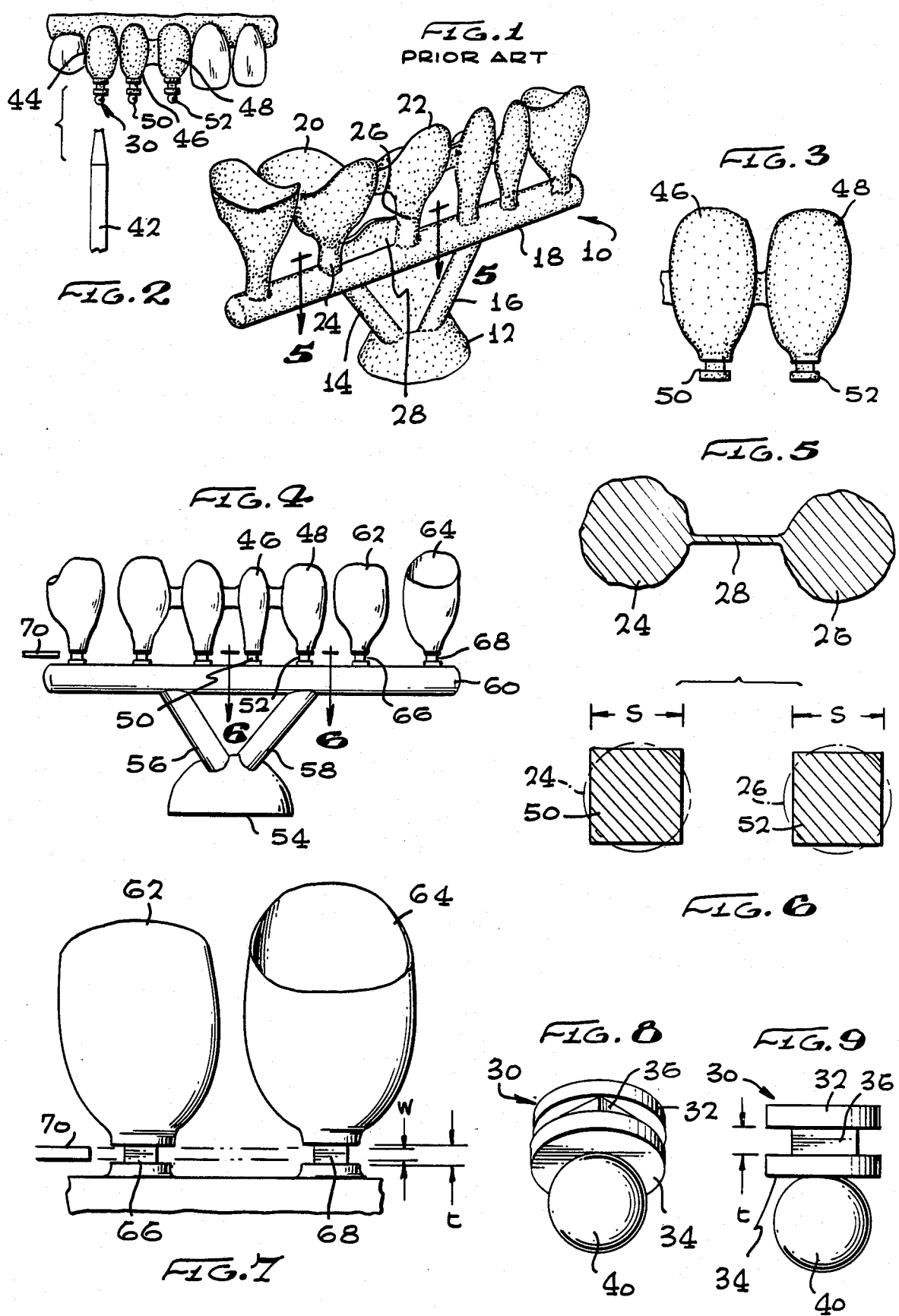

GATE

CROSS-REFERENCE

This application is a continuation-in-part of my earlier application Ser. No. 625,302 filed June 27, 1984, abandoned the entire disclosure of which is incorporated herein by this reference.

BACKGROUND OF THE INVENTION

This invention is directed to a gate for employment in the molding of dental prostheses by the lost wax molding process. The gate starts as a wax master having a feeder of square cross section for reduced stress in the investment material with a circular disc on each end thereof. The discs are attached to the prostheses and the reservoir bar. The disc shape aids filleting at these attachments.

In the conventional formation of dental prostheses, a wax master is formed of the dental part to be created. This wax master is mounted by means of a gate upon a reservoir bar. The reservoir bar, in turn, is usually connected through two feeders to a funnel-like sprue. The material from which the gate, reservoir bar and feeders are made is extruded of wax with a circular section. This rod or wire is mounted on a spool. It is provided in several different diameters so that the laboratory technician can select the appropriate cross section. He cuts a reservoir bar from the long length on the spool and cuts usually two feeder bars of the same or slightly smaller size. The feeder bars are connected to the reservoir and are connected to the sprue by means of heating sticky wax and flowing it into the joints.

A plurality of wax masters representing the metal prostheses are attached to the reservoir bar in a similar way. The wax gate extrusion of circular section is cut to length by the technician and secured to both the wax master of the prosthesis and the reservoir bar. When the wax master is complete, investment material is cast around it, the wax is removed, and liquid metal is poured into the sprue. The liquid metal moves through the reservoir bar and gates into the mold recess of the prosthesis and cools therein. As the casting of the prosthesis cools and solidifies, it is supposed to draw liquid metal from the reservoir bar and sprue through its gate into the casting. As the solidifying metal in the casting shrinks, the gate must supply molten alloy to fill in for the shrinkage of the metal. If the metal in the gate solidifies before the center of the prosthesis casting, shrinkage porosity occurs in the center of the prosthesis casting. When the gate is too long, which places the prosthesis casting recess too far from the reservoir bar, the gate will freeze before the casting. Since the present material of circular section is of indefinite length, it is the technician who is required to make the judgment of gate length when he cuts it from the reel. As a result, the gate length is inconsistent, and the importance of a short gate length is not sufficiently recognized. This is particularly true when the prosthesis is a bridge of multiple elements and the bridge is curved. In this case, the technician adjusts the gate length so that the curved bridge is fed from a straight reservoir bar. With a different gate length on each portion of the bridge, poor casting may result.

Another problem which arises from the use of gates and feeders of circular section is that when such lie adjacent each other, the facing curved surfaces produce stress raisers in the investment so that the investment cracks between adjacent gates. In usual dental laboratory practice, this happens quite often. The result is a fin of metal which joins the adjacent castings, gates and the reservoir bar. This fin ruins the castings or requires a great deal of cleanup. The rod material of circular section, supplied in great length for use to make gates, reservoir bars and feeders, is supplied in different diameters for different purposes. As noted above, the gate feeds molten metal to the casting as it cools and, as a result, larger gates are required for larger castings. For a cap for a lower tooth, a 10-gauge gate diameter is sufficient. For a pre-molar cap or an upper anterior tooth cap an 8-gauge gate is proper to feed the mold recess. Furthermore, for a cap for a posterior tooth, which is quite large, a 6-gauge gate would be appropriate to feed the molten metal from the reservoir bar. After the casting is hard and the investment material is removed, the casting must be cut free from the reservoir bar. With different gate diameters, it is difficult to judge the end of the casting, where the cut is to be made to remove the gate and not cut into the casting, and when the cutter disc is used to cut free the casting, occasionally the casting is cut instead of the gate. This requires a new casting which reduces productivity.

SUMMARY OF THE INVENTION

In order to aid in the understanding of this invention, it can be stated in essentially summary form that it is directed to a gate particularly useful for investment casting. The gate has a short feeder of square cross section with a circular disc on each end. The initial gate is supplied in wax and preferably carries a handle on one end.

It is an object and advantage of this invention to provide a gate master which can form a suitable gate area in an investment casting, with the gate being of the most desirable configuration, shape and size to permit pouring of an investment casting with minimum likelihood of cracking of the investment between adjacent gates, maximum opportunity to feed molten metal to the cooling casting, and optimum cleanup conditions.

It is a further object and advantage of this invention to provide a wax master of a gate having a feeder in the direction of metal flow through the gate which is of substantially square cross section, so that the gate may be oriented with respect to adjacent gates so that sides of the square feeders face each other to minimize stress raising to reduce the cracking of the investment between the gates.

It is a further object and advantage of this invention to provide a gate which is of square cross section in the direction of metal flow therethrough and which is of a short and uniform length in the direction of metal flow to maximize the flow area of the gate while minimizing the distance in the cutting direction to aid in the cutoff of the gate after the casting is made.

It is a further object and advantage of this invention to provide a gate of square cross section having a disc at each end thereof so that the discs may be attached to adjacent portions of the wax master and fillets are readily formed thereon to provide ease of joining and optimum conditions of metal flow, while at the same time defining the place for cutoff after the casting has been poured and the investment removed.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a perspective view of a metal investment casting made in the manner of the prior art.

FIG. 2 is a plan view of a wax master, carrying gates in accordance with this invention, for preparation of an investment for casting.

FIG. 3 is an enlarged view of a portion of the same structure as FIG. 2, with parts broken away and with the handles of the gates removed.

FIG. 4 is a front elevational view of the structure similar to FIG. 2, and showing the reservoir bar, feeder and sprue attached, and also showing the same structure in metal after an investment has been poured around the wax master, the wax removed and metal cast into the investment so that FIG. 4 also represents the corresponding metal structure.

FIG. 5 is an enlarged section taken generally along the line 5—5 of FIG. 1, with parts broken away, showing the fin between adjacent prior art gates.

FIG. 6 is an enlarged section taken generally along the line 6—6 of FIG. 4, with parts broken away, showing adjacent square gates in accordance with this invention.

FIG. 7 is an enlarged view of two of the dental prostheses of FIG. 4, showing how the gates will be cut off. In this Figure, and other similar Figures the gates are enlarged out-of-scale for ease and clarity of illustration.

FIG. 8 is a perspective view of one of the gates in accordance with this invention, when it is in wax form, with its handle attached.

FIG. 9 is a side elevational view of the gate of FIG. 8

DESCRIPTION OF THE PREFERRED EMBODIMENT

FIGS. 1 and 5 show a casting assembly which has been cast in metal by means of the lost wax process. The assembly, generally indicated at 10 in FIG. 1, is made up of a sprue 12 which is a funnel-like structure which feeds metal through a plurality of feeders such as feeders 14 and 16 to a reservoir bar 18. Mounted upon the reservoir bar are a plurality of dental prosthesis castings which need to be cut off of the reservoir bar and finished. These dental prostheses begin as wax masters which are mounted upon gates which, in turn, are mounted upon the reservoir bar 18. Tooth caps 20 and 22 are specifically indicated in FIG. 1, and these are mounted upon gates 24 and 26, respectively. As discussed in the background, the gates are cut off of a long, spooled length of wax material by the dental laboratory technician. As is seen in FIG. 5, the investment around the wax material is cracked to leave a fin 28 of thin metal between the adjacent gates. Cracking of the investment in this location is common and is caused by the stress raiser created by the facing convex surfaces of adjacent round gates. When the crack in the investment extends to the space in which the dental prosthesis is to be cast, then the fin also adjoins the dental prosthesis casting. The presence of this fin extends the time required to finish the dental prosthesis and uses additional metal. Thus, the fin is undesirable. In addition, the transition between the sprue and the dental prosthesis is indefinite, as seen in FIG. 1. Thus, it is difficult to cut off the sprue as close as possible to the prosthesis without cutting into the prosthesis. This also extends preparation time and unnecessarily uses metal. Thus, FIGS. 1 and 5 illustrate the conditions discussed in the background above.

The gate 30 is the preferred embodiment of the gate in accordance with this invention. The gate 30 is shown in its wax configuration in FIGS. 2, 8 and 9. Gate 30 comprises upper and lower discs 32 and 34 joined by square feeder 36. The discs are in the form of right circular cylinders, and the square feeder is preferably square in cross section on a plane parallel to the end planes of the discs.

The lateral size of each gate is primarily dictated by the volume of liquid casting metal which will flow through the gate to form the prosthesis casting, and thus is dictated by the size of the prosthesis casting. To satisfy the needs of modern prosthesis casting practice, gates of various sizes having sides "s", see FIG. 6, in the dimensions $\frac{1}{2}$ mm, $1\frac{1}{4}$ mm, $1\frac{3}{4}$ mm, $2\frac{1}{2}$ mm and 4 mm are provided. In the preferred embodiment, the height "t" dimension of each of the discs and the square feeder are 1 millimeter in thickness in the direction of the axis of the discs, which are in alignment. The height of the gate in the flow direction is minimized to limit restriction and is uniform between gates for casting uniformity, and for removal uniformity as described below. The square feeder is arranged symmetrically on that axis.

The diameter of the discs 32 and 34 is equal to or slightly larger than the diagonal dimension of the square gate 36. Thus, the diameter of the discs is approximately 1.414×s. Variations from this preferred diameter are on the high side. This preferred disc diameter is preferable because it permits attachment with a good fillet, consistent with the size of the casting to be fed by the gate and minimum material to be later ground off during finishing. The gate 30, thus described, is made of wax and must be handled to be put in place.

A convenient way of handling the gate is to provide sphere 40 integrally formed therewith. This sphere can be engaged with a manual handle, as taught in my earlier application Ser. No. 625,302, filed June 27, 1984. The handle disclosed therein is generally indicated at 42 in FIG. 2. The handle 42 permits manual pickup of the gate 30. The gate is picked up by means of handle 42 or any other convenient way and is attached to a wax master of the configuration of the desired dental prosthesis. In the present case, wax masters 44, 46, and 48 of particular dental prostheses are shown in FIG. 2. Gate 30 is secured to wax master 44 by the employment of conventional sticky wax and heat. The wax is applied around the upper disc of the gate in order to provide the desired fillet, as will be discussed below. Gates 50 and 52 are respectively attached to the wax masters 46 and 48, again by the use of sticky wax and heat to provide attachment and filleting. The specific disc size related to prosthesis size aids in good filleting. The wax masters 46 and 48, as seen in FIGS. 2 and 3, are attached together to form a portion of a dental prosthesis bridge. In FIG. 3, the structure is still in wax form and the spheres are cut off of the gates 50 and 52 so that the lower disc of each of the gates may be attached to a reservoir bar.

The structure in FIG. 4 starts out as a wax assembly of sprue 54, feeders 56 and 58, and reservoir bar 60. This assembly can be supplied as a one-piece wax assembly, or can be formed of a sprue together with wax rods which are secured together to form the configuration. When assembled, the wax masters corresponding to the desired dental prostheses are secured thereto. As is seen in FIG. 4, the wax masters 46 and 48 of corresponding dental prostheses are mounted upon the reservoir bar 60 by means of attachment of their corresponding gates 50 and 52 to the reservoir bar 60. Again, attachment is made by means of the application of sticky wax and heat to attach the sprues to the reservoir bar. Furthermore, the lower discs of each of these gates is filleted with respect to the reservoir bar. It is important to note that the gates are oriented so that the square sides of the square feeder in the middle of each gate face each other. The square feeders are arranged so that the faces of the square feeders are substantially normal to a line connecting the central axes of adjacent gates. This results in an orientation as indicated in FIG. 6 which prevents a stress raiser from being present and minimizes the potential for cracking between adjacent gates. In addition to the attachment of wax masters 46 and 48 upon reservoir bar 60, wax masters 62 and 64 of desired dental prostheses are respectively mounted on gates 66 and 68. These gates, in turn, are secured to the reservoir bar 60. FIG. 7 shows in more detail the manner in which filleting is accomplished around the upper and lower discs on the wax reservoirs.

FIG. 4 starts by representing the creation of the wax master of the various dental prostheses, together with the necessary feeders and gates to supply metal to produce a corresponding metal casting. Investment material is placed around the wax master and the investment material hardens and dries. It is during this stage that cracking would occur between adjacent gates, but with the gates arranged with their flat sides toward each other, stress raising is minimized and cracking is minimized. By having the gate sides face each other, the distance between the gates is maximized and there are no facing curves to concentrate stress. Furthermore, since the square feet or portion of the gates is oriented in that manner, the gate flow area is maximized at the same time the distance between the gates is maximized for a particular flow area through the square feeder of the gates. As the casting cools and the molten metal solidifies, the metallic structure shrinks. This requires feeding liquid metal through the gates from the reservoir bar to provide molten metal during the solidification process in order to prevent porosity in the finished casting. The short length of the square feeder and the uniform length thereof permits reliable feeding during solidification. After solidification, the investment material is removed and the metal casting is revealed. The structure of FIGS. 4, 6 and 7 is structurally the same in metal as it had been in wax. Therefore, FIGS. 4, 6 and 7 can also serve to disclose the handling of the metal casting assembly and the removal of the dental prostheses from the reservoir bar 60.

FIGS. 4 and 7 illustrate individual caps 62 and 64 on their gates 66 and 68. In the metallic condition, the prostheses must be cut off of the reservoir bar. In FIGS. 4 and 7, the edge of cutting wheel 70 is shown. The dental laboratory technician lines up the cutting wheel with the square feeder in the gates and moves the wheel through the square feeders. First of all, the square feeders clearly indicate to the dental laboratory technician where the cut should occur for removal of most of the gate and without the cutting into the body of the dental prosthesis. This is because the square feeder is smaller than the upper disc to clearly delineate the transition from feeder to upper disc. In addition, it can be appreciated that, for such small cuts, it is the wheel feed distance which is critical rather than the area being cut. This demonstrates another advantage of the use of the square feeder. The square feeder maximizes the area through which molten metal can flow to the casting and minimizes the feed distance through which the cutting wheel moves, parallel to one of the faces. The distance "s" in FIG. 6 illustrates the distance the wheel 70 must be fed to accomplish cutoff, and this distance is shorter than the cutting wheel feed distance which would be required if the square feeders were circular, as illustrated in dashed lines in FIG. 6.

The preferred height of "t" of the square feeder is 1 millimeter, as discussed above, and the cutting wheel 70 has a thickness "w" which is less than the height of the square feeder, as illustrated in FIG. 7. In this way, the square feeder provides an accurate guide for the dental laboratory technician so that he may cut the prosthesis off of the reservoir bar within a millimeter of the dental prosthesis without danger of cutting into the dental prosthesis.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A dental prosthesis assembly comprising:
   a reservoir bar;
   at least one dental prosthesis structure positioned adjacent said reservoir bar and a gate interconnecting said dental prosthesis and said reservoir bar, the improvement comprising:
   said gate being configured with first and second members spaced from each other a predetermined distance and a feeder therebetween, said first member being secured to said dental prosthesis and said second member being secured to said reservoir, said feeder being a predetermined and uniform cross section and of smaller cross section than either said first or said second member.

2. The assembly of claim 1 wherein at least one of said first and second members is substantially in the form of a right circular cylinder so as to be in the form of a disc.

3. The assembly of claim 2 wherein
   both said first and second members are substantially in the shape of a right circular cylinder so that said first and second members are respectively first and second discs.

4. The assembly of claim 1 wherein said feeder has a substantially square cross section.

5. The assembly of claim 3 wherein said feeder has a substantially square cross section.

6. The assembly of claim 3 wherein said first disc is secured to said prosthesis and is filleted thereto and said second disc is secured to said reservoir bar and is filleted thereto.

7. The assembly of claim 1 wherein
   there is a plurality of prostheses positioned along the length of said reservoir bar, each prosthesis being secured to said reservoir by one of said gates with said gates spaced from each other.

8. The assembly of claim 7 wherein
   said feeder of each of said gates has a substantially square uniform cross section and is of predetermined length.

9. The assembly of claim 8 wherein the faces of adjacent square feeders face each other to maximize the distance between said feeders and to minimize stress raising between adjacent feeders.

10. The assembly of claim 7 wherein said assembly is cast of metal and said feeders lie substantially in a line so that they may be quickly and accurately cut.

11. The assembly of claim 5 wherein said assembly is made of wax for use with a lost wax process for casting.

12. The method of making a dental prosthesis comprising the steps of:
    mounting a wax gate structure having first and second members and a feeder of constant cross section and of fixed length therebetween with its first member secured and filleted to a wax master of a dental prosthesis;
    mounting the second member on a wax reservoir bar including filleting the second member to the reservoir bar;
    investing the wax, removing the wax from the investment, pouring metal into the investment and removing the investment to expose a metal dental prosthesis mounted on the gate on the reservoir bar; and
    cutting through the feeder in the gate to remove the metal dental prosthesis from the reservoir bar to avoid cutting the metal dental prosthesis.

13. The method of claim 12 further including the step of:
    mounting a plurality of wax models of dental prostheses along the length of the reservoir bar, each on its own gate, with the first and second members of each gate respectively filleted to the wax model of the dental prosthesis and the reservoir bar, with the feeder between the first and second members in alignment along the length of the reservoir bar, and further including the final step of:
    cutting all of the metal gates at the feeder between the members.

14. The method of claim 12 wherein
    there is a plurality of wax master dental prostheses and a gate for each prosthesis with the gate having a square feeder between its first and second members, and further including the step of:
    mounting the gate on the wax dental prostheses and on the reservoir bar so that the sides of the square feeders face each other to maximize the distance therebetween.

15. The method of claim 12 wherein each of the first and second members is a disc and the method includes the step of filleting the first disc with respect to the dental prostheses and the second disc with respect to the feeder bar.

16. The method of claim 15 wherein
    there is a plurality of wax master dental prostheses and a gate for each prosthesis with the gate having a square feeder between its first and second members, and further including the step of:
    mounting the gate on the wax dental prostheses and on the reservoir bar so that the sides of the square feeders face each other to maximize the distance therebetween.

17. The method of claim 12 wherein the gate is provided with a handle and further including the step of grasping the handle to maneuver and position the gate while the first member is secured to the dental prosthesis.

18. The method of claim 17 further including the step of removing the handle before attachment of the second member to the reservoir bar.

19. The method of claim 17 wherein the handle is a sphere secured to the lower member and the gate is handled by grasping the sphere in a manually operable grasping device.

20. A gate comprising:
    a first member for attachment to a dental prostheseis;
    a second member for attachment to a reservoir bar; and
    a feeder between said first and second members, said feeder being of constant cross section and of smaller cross section than said first and second members to define the feed area through said gate.

21. The gate of claim 20 wherein said feeder has a substantially square cross section.

22. The gate of claim 20 wherein at least one of said first and second members is substantially in the form of a right circular cylinder having an axis so that it is in the form of a disc.

23. The gate of claim 20 wherein each said first and second member is in the form of a right circular cylinder having an axis with said axis of each cylinder lying together so as to form two discs spaced from each other by said feeder.

24. The gate of claim 23 wherein said feeder has a substantially square cross section.

25. The gate of claim 24 wherein said gate is made of wax so that it may be employed in investment casting.

26. The gate of claim 25 wherein a handle is secured to said gate so that said handle may be grasped and the gate maneuvered so that at least one of its discs can be secured.

27. The gate of claim 26 wherein said handle is a sphere.

28. The gate of claim 26 wherein said handle is positioned adjacent said second disc so that said handle is removed after attachment of said first disc and before attachment of said second disc.

* * * * *